(12) United States Patent
Calvosa et al.

(10) Patent No.: US 8,182,513 B2
(45) Date of Patent: May 22, 2012

(54) MODULAR VERTEBRAL STABILIZER

(75) Inventors: Giuseppe Calvosa, Pisa (IT); Miria Tenucci, Lucca (IT)

(73) Assignee: Lanx, s.r.l., Medolla (IT)

( * ) Notice: Subject to any disclaimer, the term of this patent is extended or adjusted under 35 U.S.C. 154(b) by 761 days.

(21) Appl. No.: 12/094,732

(22) PCT Filed: Nov. 24, 2006

(86) PCT No.: PCT/IB2006/003342
§ 371 (c)(1),
(2), (4) Date: May 22, 2008

(87) PCT Pub. No.: WO2007/060534
PCT Pub. Date: May 31, 2007

(65) Prior Publication Data
US 2008/0262546 A1    Oct. 23, 2008

(30) Foreign Application Priority Data

Nov. 24, 2005  (IT) ................. PI2005A0126
Jan. 2, 2006   (IT) ................. PI2006A0001

(51) Int. Cl.
*A61B 17/70* (2006.01)
*A61B 17/04* (2006.01)

(52) U.S. Cl. ......... 606/250; 606/246; 606/263; 606/301

(58) Field of Classification Search .............. 606/246, 606/250, 256, 300, 308, 269, 270, 265, 263, 606/251, 253, 254, 86 A
See application file for complete search history.

(56) References Cited

U.S. PATENT DOCUMENTS

| | | | | |
|---|---|---|---|---|
| 5,476,465 A | * | 12/1995 | Preissman | 606/279 |
| 5,562,660 A | * | 10/1996 | Grob | 606/258 |
| 7,611,518 B2 | * | 11/2009 | Walder et al. | 606/86 A |
| 2004/0111088 A1 | * | 6/2004 | Picetti et al. | 606/61 |
| 2005/0059972 A1 | * | 3/2005 | Biscup | 606/73 |
| 2005/0154390 A1 | | 7/2005 | Biedermann et al. | |

FOREIGN PATENT DOCUMENTS

| | | | |
|---|---|---|---|
| EP | 0 669 109 A1 | 8/1995 | |
| EP | 0669109 | * 8/1995 | 606/250 |
| EP | 1 430 846 A1 | 6/2004 | |

* cited by examiner

*Primary Examiner* — Pedro Philogene
(74) *Attorney, Agent, or Firm* — Holland & Hart LLP

(57) ABSTRACT

A spinal stabilization device allowing motion between adjacent vertebrae is provided. The spinal stabilization device connects at least two adjacent vertebrae using an elongated block operatively connected or compressed between the heads of two screws connected to the adjacent vertebrae. The head and the screw may be separate such that they may be componible together. A resilient tie-member is connected between two heads to keep the block in position. The tie-member is in tension to maintain the elongated block compressed. The spinal stabilization device may have a transversal tie-member that connects between the heads of two screws transverse and diagonal with respect to the spinal column.

19 Claims, 10 Drawing Sheets

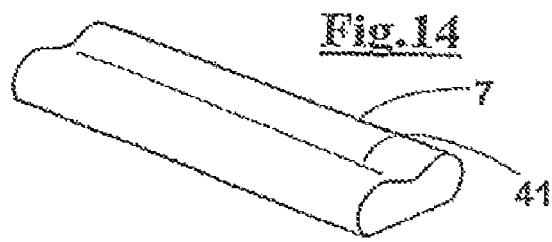
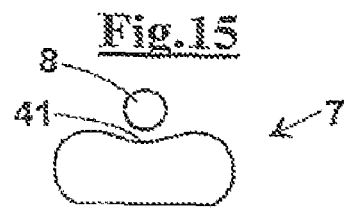
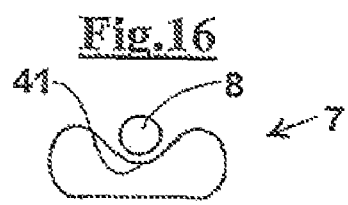
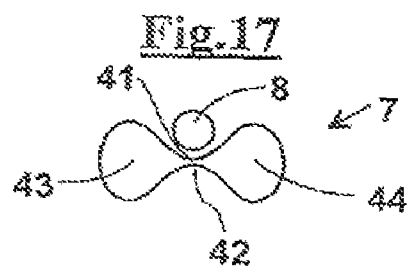
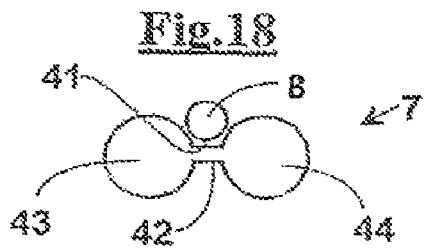
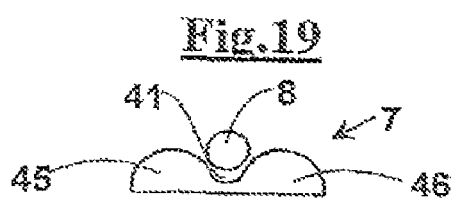
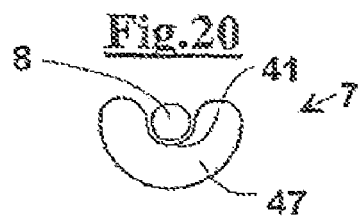
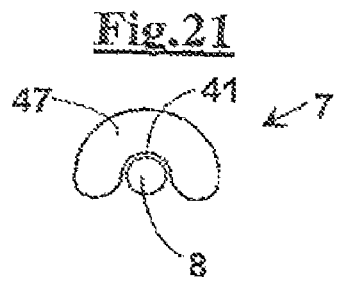
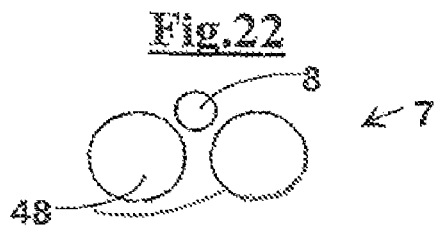

MODULAR VERTEBRAL STABILIZER

FIELD OF THE INVENTION

The present invention relates to the medical/surgical field and more precisely it relates to a stabilizer of the spinal column, which is adapted to connect to each other at least two adjacent vertebrae using flexible and/or stiff connection elements that allow for some limited motion to the vertebrae.

Furthermore, the invention relates to a connecting element for stabilizers of the spinal column, in particular flexible or dynamic stabilizers, i.e. that allow for some limited motion to the vertebrae, and/or stiff stabilizers, i.e. that block the movement between at least two vertebrae.

DESCRIPTION OF THE PRIOR ART

Many pathologies relative to the functionality of the spinal column are cured by total or partial immobilization, in particular, with a technique so-called "intervertebral arthrodesis", with the use of connecting means and/or with the addition of portions of bone tissue, which perform a union between such adjacent vertebrae.

In the prior art vertebral stabilizing devices of the type either static or dynamic are known, having a screw adapted to be connected to a vertebra, and stiff elements or elements with limited mobility, having two ends integral to two screws connected to two adjacent vertebrae.

In particular, a dynamic stabilizing device, capable of allowing for a relative movement between the vertebrae that is resiliently limited and blocks an approaching below a predetermined distance, is described in EP0669109 in the name of Dubois. This vertebral stabilizer comprises a spacing body, resistant to compression and adapted to transfer forces between two screws implanted in respective vertebrae, and a tensioning cord connected between the above described screws and passing in an inner longitudinal recess obtained in said spacing body.

Such a stabilizer has the drawback of being directly assembled locally on the spinal column after having inserted the screws in the vertebrae, with open surgery in a space close to the vertebra. Therefore, there is a high invasivity in the operation on the patient, because enough space has to be created close to the vertebra for carrying out assembling steps, and high difficulty to the surgeon that has to arrange and assemble each single element directly on the vertebrae.

Another drawback of the above described stabilizer is that it does not allow a transversal connection between screws mounted on different vertebrae for transmitting forces in a diagonal direction with respect to the axis of the spinal column.

A further drawback of this device is that the tensioning cord has to be threaded in the spacing body, and this requires a higher effort for the surgeon.

In some cases, furthermore, the need is felt to assemble on a same stabilizer both static portions and dynamic stabilizing portions, creating a hybrid stabilizer, wherein such portions can be chosen by the surgeon according to the characteristics of the pathology.

Furthermore, the need is felt of a vertebral stabilizer that allows the change or the recomposition of some portions of the stabilizer without extracting the screws.

It is furthermore, presently disadvantageous to convert a vertebral dynamic stabilizer into a static stabilizer or vice-versa, without loosening the screws already implanted in the vertebrae, with a remarkably invasive operation.

SUMMARY OF THE INVENTION

It is then a feature of the present invention to provide a vertebral stabilizer of dynamic and modular type, adapted to be assembled separately from the spinal column and then mounted on the spinal column in a few seconds.

Another feature of the present invention is to provide a vertebral dynamic stabilizer that allows the transversal connection between adjacent vertebrae, in order to transmit forces in a diagonal direction between screws of adjacent vertebrae, to limit the relative rotation between adjacent vertebrae, such as for pathologies with vertebral rotation like scoliosis and congenital and acquired vertebral rotations.

A further feature of the present invention is to provide a stiff vertebral stabilizer, adapted to be assembled separately from the spinal column and then mounted on the spinal column very quickly.

It is another feature of the present invention to provide a vertebral stabilizer for converting a dynamic stabilizer into a static stabilizer without loosening the screws already implanted in the vertebrae.

Another feature of the present invention is to provide a stiff vertebral stabilizer that allows the connection to a vertebral dynamic stabilizer, giving rise to a hybrid stabilizer.

These and other objects are achieved by a vertebral stabilizer comprising:
  an elongated block, having two ends and a predetermined length extending between said two ends,
  a screw adapted to be put in a vertebra, said screw having a head;
  means for keeping said block compressed between two of said heads in order to keep said screws at a predetermined distance from each other,
wherein said head is separated from said screw, said head and said screw being componible together by engagement means provided between said head and said screw.

In particular, said engagement means comprises a connection selected from the group comprised of:
  a click engagement comprising resilient engagement means;
  an engagement with threaded surfaces;
  by screws;
  a bayonet coupling;
  a retainer means.

According to another aspect of the invention, such objects are achieved by a vertebral stabilizer comprising:
  a resilient flexible tie-member, in particular, a wire, capable of bearing a predetermined tension;
wherein said through hole and said housing are made in said head such that said block is kept compressed between two of said heads, said block having its ends engaging with the respective housings in order to keep said screws at a predetermined distance from each other, said wire resulting stretched between said two heads and external to said block.

This way, the operations are simpler of assembling the block between two heads, it being unnecessary to thread the wire in the spacing element.

In particular, said first through hole is made in said housing and said block has a longitudinal channel adapted to receive said tie-member parallel to said block.

Alternatively, said through hole is obtained in said head outside of said housing.

In a preferred exemplary embodiment, said head has two housings for engagement of the block made on two opposite faces of said heads.

Advantageously, said head comprises at least one second through hole, at an angle with respect to said first hole, incident to the axis of said screw, said second hole being adapted to house a transversal connecting tie-member, diagonally with respect to the spinal column, the heads of two of said screws being applied to two adjacent vertebrae. This way, said transversal tie-member does not apply any torque to said head avoiding the rotation of the head same.

Advantageously, means are provided for fastening said resilient flexible tie-member and said resilient transversal tie-member to said head, by making an enlargement on said wire that prevents it from passing through said hole.

In particular, said fastening means, by making an enlargement on the wire, are selected from the group comprised of:
- at least one deformed ring clamped about said wire, said ring penetrating partially in the cross section of said wire when plied;
- a tubular element deformable by compression;
- a deformable element having teeth capable of penetrating in the cross section of said wire when said element is squeezed;
- a snap-hook that can be clamped on said wire;
- a knot;
- an enlargement of the wire by plastic deformation.

In an alternative exemplary embodiment, said fastening means comprises at least one screw gripping said wire.

In a particular exemplary embodiment, said head comprises a countersunk portion or enlarged opening at least at one end of said through hole, said countersunk portion being adapted to contain said fastening means, once applied to said pulling element, so that said fastening means are capable of entering said countersunk portion but not of passing through said hole.

Advantageously, said elongated block is made of resilient and flexible material.

In particular, said elongated block has shape selected from the group comprised of:
- a prismatic body having a substantially rectangular base with a longitudinal channel made on a outer side surface;
- a prismatic body having a substantially rectangular base with a longitudinal channel made on both larger side surfaces;
- a prismatic body having base substantially as a half circular crown;
- two prismatic bodies parallel to each other, in particular, substantially cylindrical, connected by a narrow strip;
- two prismatic bodies parallel to each other, substantially cylindrical, different from each other.

In an advantageous exemplary embodiment, said head is obtained separated from said screw, said head and said screw being componible together by engagement means provided between said head and said screw.

This way, the surgeon can implant the screws on the bone tissue in the predetermined position. Then, the surgeon can put on the screws, which are suitably kept distant from each other, the heads with the relative block and wire tie-member being suitably tensioned.

It is thus possible, for the surgeon, to pre-assemble the heads, with the relative block and with the tensioned wire, apart from the operation field, reducing the operation to the simple application of the screws, to their distancing and to snap fitting the pre-assembled parts. This solution is surgically advantageous and limits to the minimum the duration of the operation on the patient.

In an advantageous exemplary embodiment, said head comprises at least one second through hole, at an angle with respect to said first hole, incident to the axis of said screw, said second hole being adapted to house a transversal tie-member connecting diagonally with respect to the spinal column the heads of two of said screws being applied to two adjacent vertebrae.

According to another further aspect of the invention, the above described objects are achieved by a vertebral dynamic stabilizer comprising:
- an elongated block, having two ends and a predetermined length extending between said two ends;
- a screw adapted to be put in a vertebra, said screw having a head having a first through hole and at least one housing at one end of said block;
- a resilient flexible tie-member, in particular, a wire capable of bearing a predetermined tension;

wherein said through hole and said housing are made in said head such that said block is kept compressed between two of said heads, said block having its ends engaging with the respective housings in order to keep said screws at a predetermined distance from each other, said wire resulting stretched between said two heads, wherein said head comprises at least one second through hole, at an angle with respect to said first hole, incident to the axis of said screw, said second hole being adapted to house a transversal tie-member connecting diagonally with respect to the spinal column the heads of two of said screws being applied to two adjacent vertebrae.

Advantageously, said head is obtained separated from said screw, said head and said screw being componible together by engagement means provided between said head and said screw.

According to a further aspect of the invention, a vertebral stabilizer according to the invention comprises:
- an elongated block, having two ends and a predetermined length extending between said two ends;
- a screw adapted to be put in a vertebra, said screw having a head having at least one housing at one end of said block;
- said housing being made in said head such that said block is kept compressed between two of said heads, said block having its ends engaging with the respective housings in order to keep said screws at a predetermined distance from each other;
- said head having means for locking said block in said housing;
- said head being obtained separated from said screw, said head and said screw being componible together by engagement means provided between said head and said screw.

In a way similar to the case as above defined, it is thus possible for the surgeon to pre-assemble the heads with the relative block tightened apart from the operation field, even without wires, reducing the operation to the simple application of the screws, to their distancing and to snap fitting the pre-assembled parts.

Advantageously, said head has a hole for passage of a resilient flexible tie-member, in particular, a wire capable of bearing a predetermined tension and an enlargement of closure on the other hand. This way, the head can house at the same time a flexible block, on one side, and a stiff block, on the other side, forming a hybrid equipment.

BRIEF DESCRIPTION OF THE DRAWINGS

The invention will be made clearer with the description of some its exemplary embodiments, exemplifying but not limitative, with reference to the attached drawings wherein:

FIG. 14 shows a perspective view of a possible exemplary embodiment of a block according to the invention;

Figure 23:
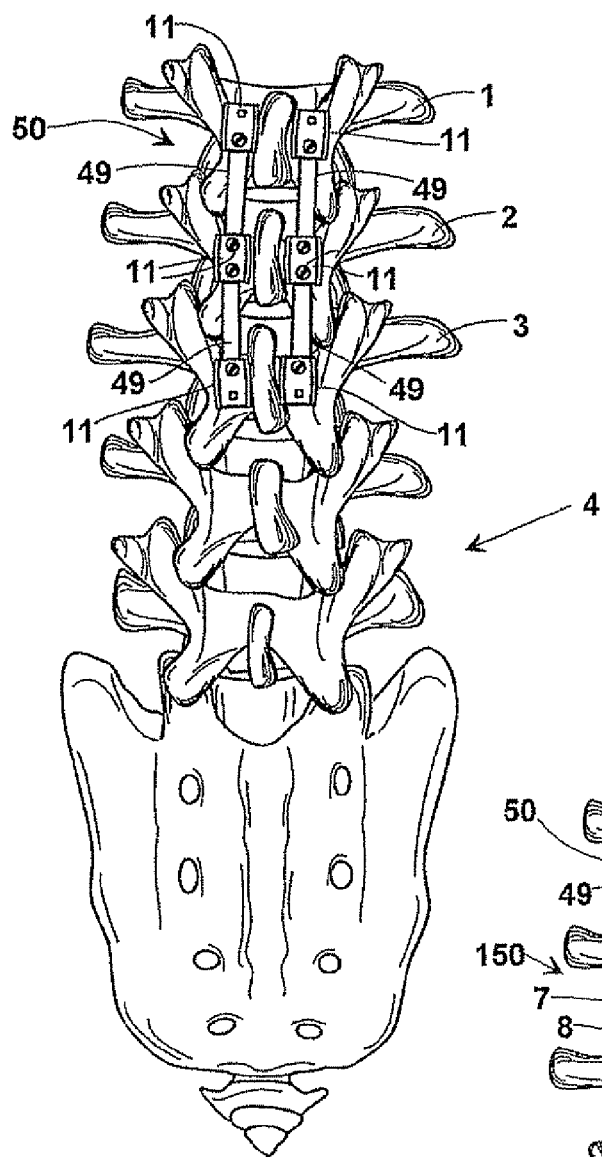
Figure 24:
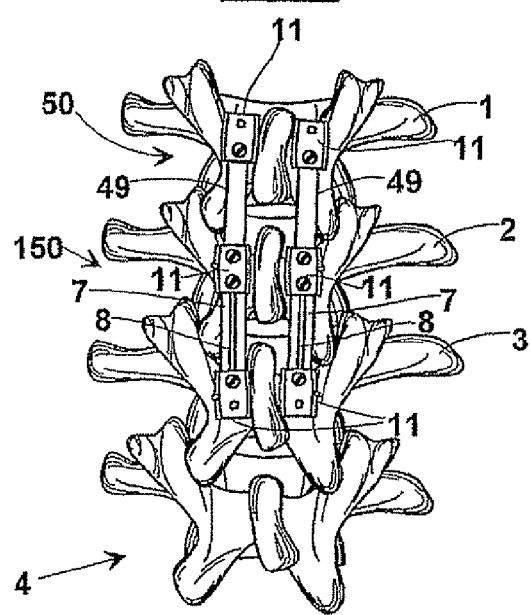
Figure 25:
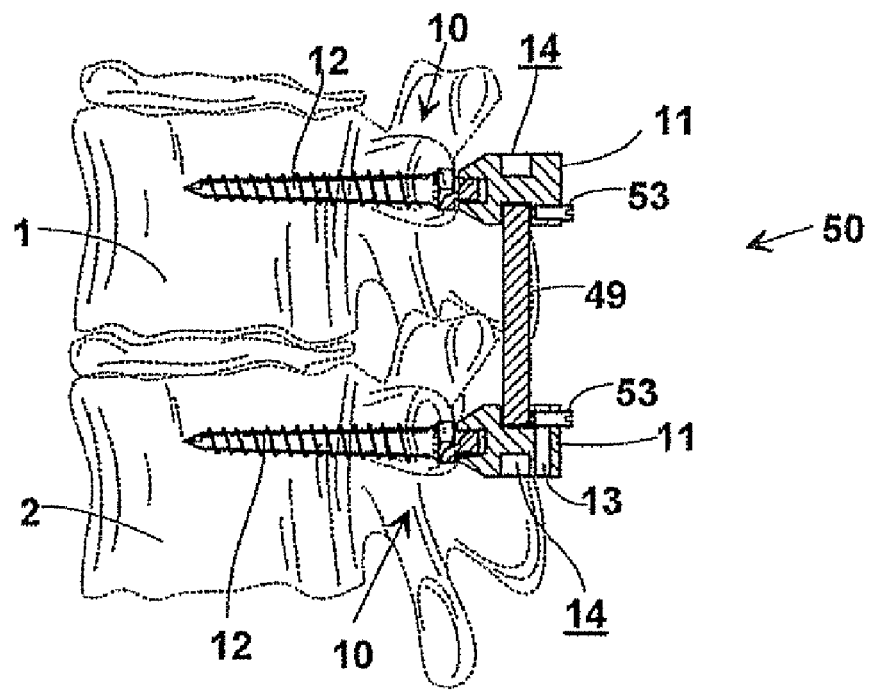
Figure 26:
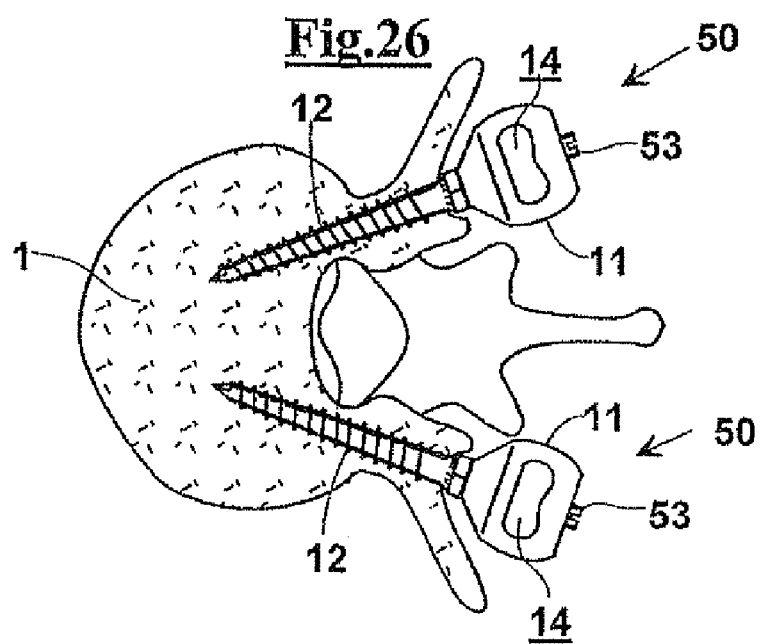
Figure 27:
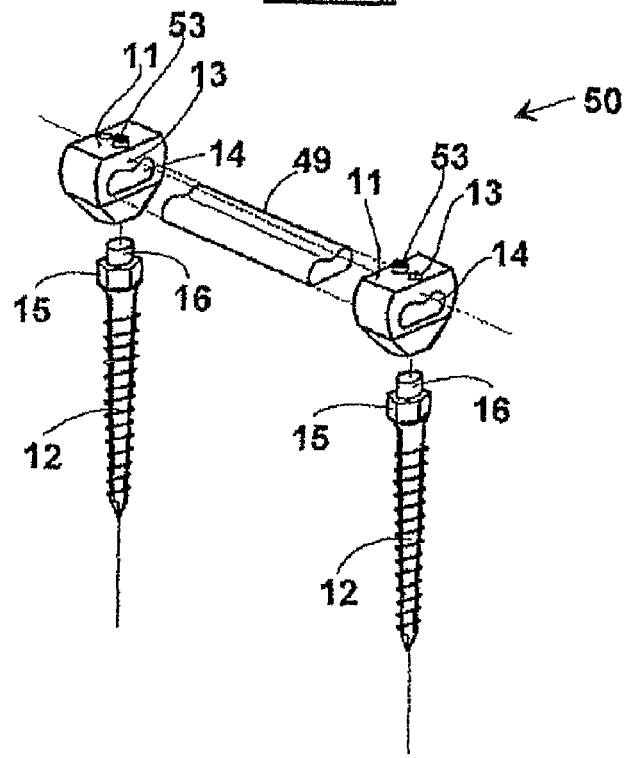
Figure 28:
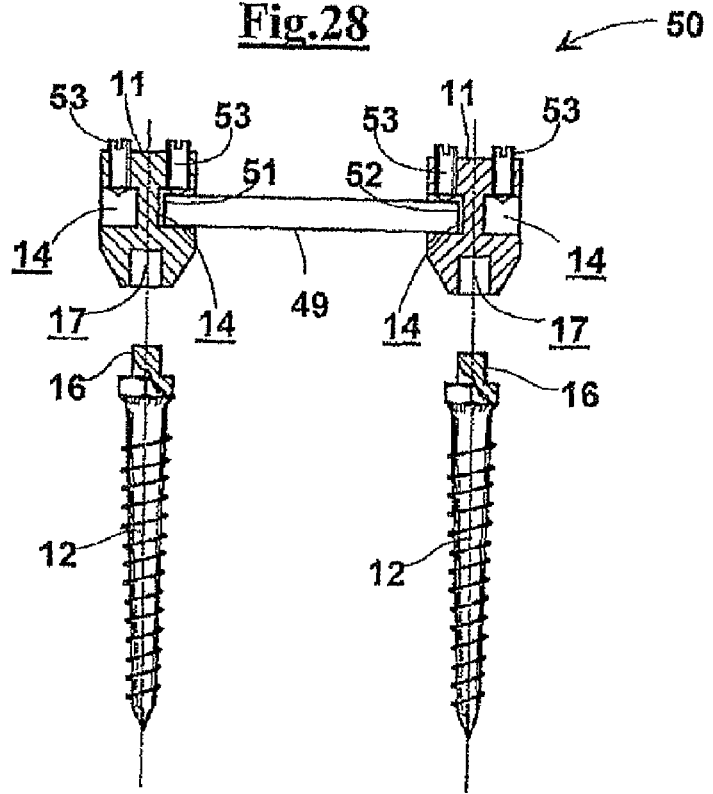
Figure 33:
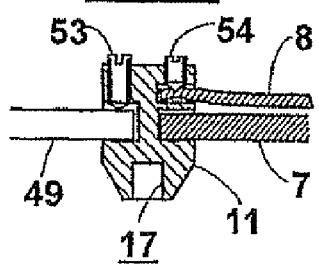
Figure 34:
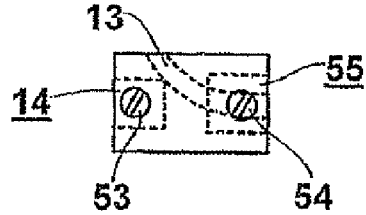
Figure 35:
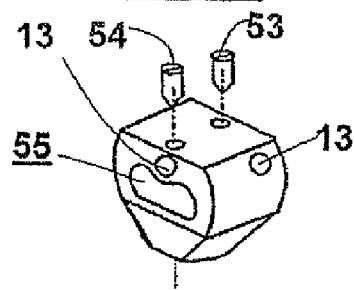

Figures from 15 to 22 show cross sectional views of respective exemplary embodiments of a block and the corresponding relative position of a pulling element;

FIG. 23 shows a front view of an example of application of a stabilizer, according to the invention, to three adjacent vertebrae;

FIG. 24 shows an exemplary embodiment of application of a stabilizer, according to the invention, to three adjacent vertebrae, by a stabilizer hybrid consisting of a combination of a dynamic stabilizer and a static stabilizer;

FIG. 25 shows a cross sectional view made with a longitudinal plane of a stabilizer according to the invention, mounted on two consecutive vertebrae;

FIG. 26 shows a cross sectional view of two such stabilizers applied to a vertebra;

FIGS. 27 and 28 show respectively an exploded view and a perspective view of a further example of stabilizer according to the invention;

FIGS. 29-32 show a cross sectional view of some possible exemplary embodiments of a head of a screw according to the invention, with one or two recesses adapted to retain a stiff block;

FIGS. 33, 34, and 35 show respectively a cross sectional, top plan and a perspective view of an exemplary embodiment of a head adapted to fasten both a stiff block, with function of static stabilizer, and an an elongated block with resilient flexible tie-member with function of dynamic stabilizer, to provide the configuration of FIG. 24.

DESCRIPTION OF PREFERRED EXEMPLARY EMBODIMENTS

Figure 1:
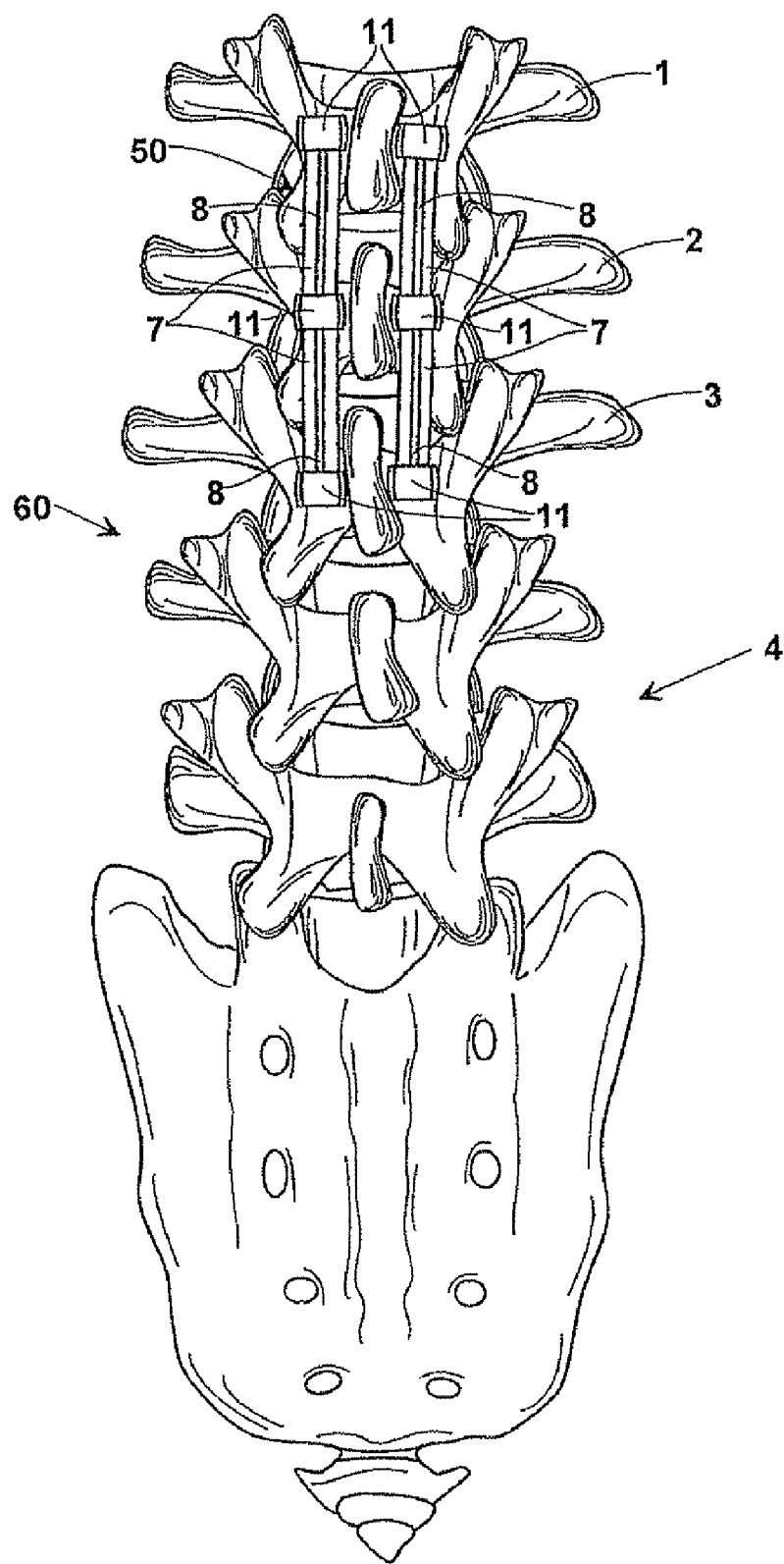
FIG. 1 shows a front view of an example of application of a dynamic stabilizer, according to the invention, to three adjacent vertebrae.

In the following description an example will be illustrated of a stabilizer of the spinal column according to the invention, adapted to connect to each other at least two adjacent vertebrae using flexible connection elements, that allow for some limited motion to the vertebrae and/or using stiff connection elements. In particular, the stabilizer, if required by the pathology, such as scoliosis and vertebral rotation, connects also diagonally two adjacent vertebrae, controlling thus the relative rotation of the vertebrae. In this connection, FIG. 1 shows two couples of stabilizers 50 and 60 applied to a spinal column 4 and, in particular, to three consecutive vertebrae 1, 2 and 3.

The stabilizers 50 and 60 comprise blocks 7 mounted and compressed between heads 11 by external resilient pulling elements 8.

Figure 2:
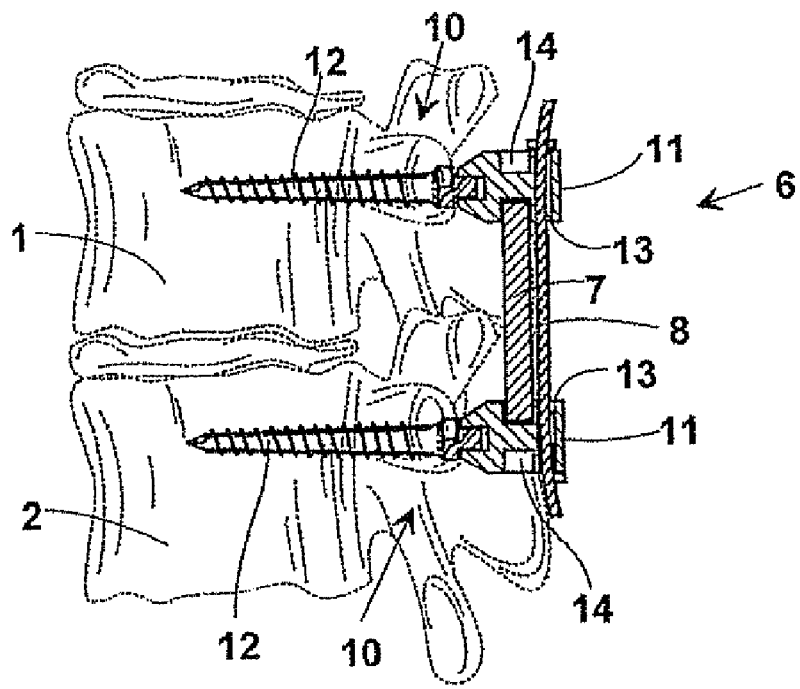
FIG. 2 shows a cross sectional view made with a longitudinal plane, of a dynamic stabilizer according to the invention, mounted on two consecutive vertebrae.

FIG. 2 shows a cross sectional view of a vertebral dynamic stabilizer 6 according to the invention, mounted on two adjacent vertebrae 1 and 2. Stabilizer 6 comprises two screws 12 applied respectively to vertebrae 1 and 2, each screw 12 supporting a respective head 11 having one or two opposite openings 14 at the end of a block 7 that house the ends of block 7. Heads 11 have a through hole 13 for a resilient flexible tie-member 8 to pass through, which tie-member, after having been tensioned between heads 11, is retained by a deformable ring 9 clamped on each tie-member end.

Figure 6:
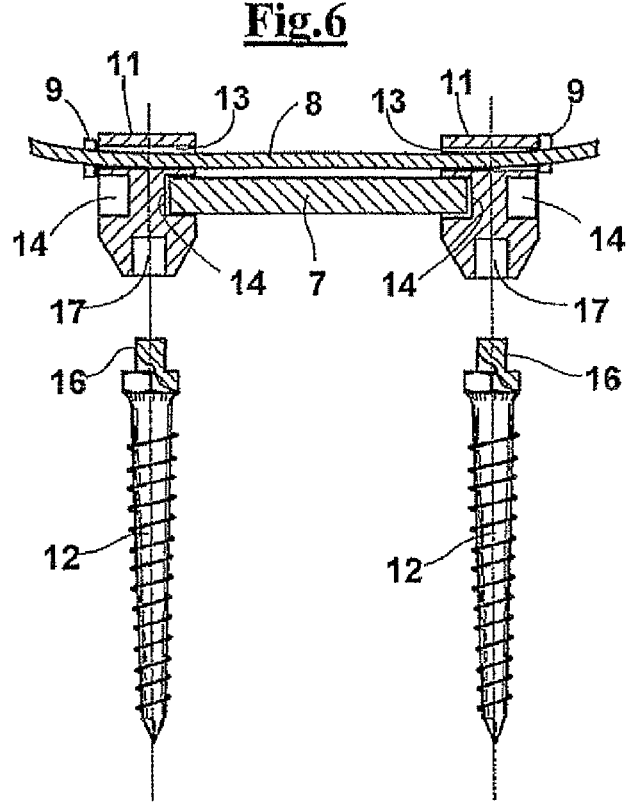
FIG. 6 shows, a longitudinal cross section of an exemplary embodiment of the present invention, which shows how the heads, the block and the wire can be pre-assembled together independently from the screws.

As shown in FIGS. 6 and 28, each head 11 has a housing 17 adapted to house the end 16 of screw 12. The shapes of the end 16 of screw 12 and of the housing 17 of head 11 are complementary and adapted to provide a snap engagement or another releasable connection, with means known in the art and not shown in detail.

Such a system allows to implant screws 12 independently from stabilizer 50. This way, the assembling steps can be made separately, respecting the relative positions of screws 12, and applied once assembled so that each head 11 is connected to a respective screw 12. This way, a less invasive assembling process is obtained with respect to the known systems, since the existing implant screws that are integral with the respective heads force the components of the stabilizer directly on the spinal column, with the need of a large open operation field owing to complex assembling operations.

Figure 3:
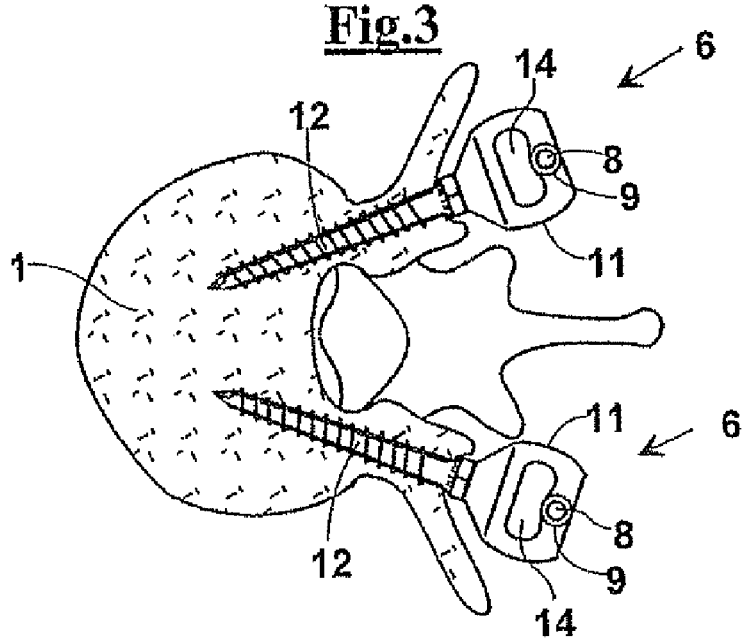
FIG. 3 shows a cross sectional view of two such stabilizers applied to a spinal column.

FIG. 3 shows a cross sectional view of two stabilizers 6 applied to two adjacent vertebrae of a spinal column, of which a vertebra 1 is visible. Screws 12 have to be implanted in order to remain completely in the bone avoiding the risk of affecting the bone marrow. In FIG. 3, each head 11 is shown with an opening 14, a wire 8 and a deformed locking ring 9 for blocking wire 8 in order to prevent it from passing through head 11.

Figure 4:
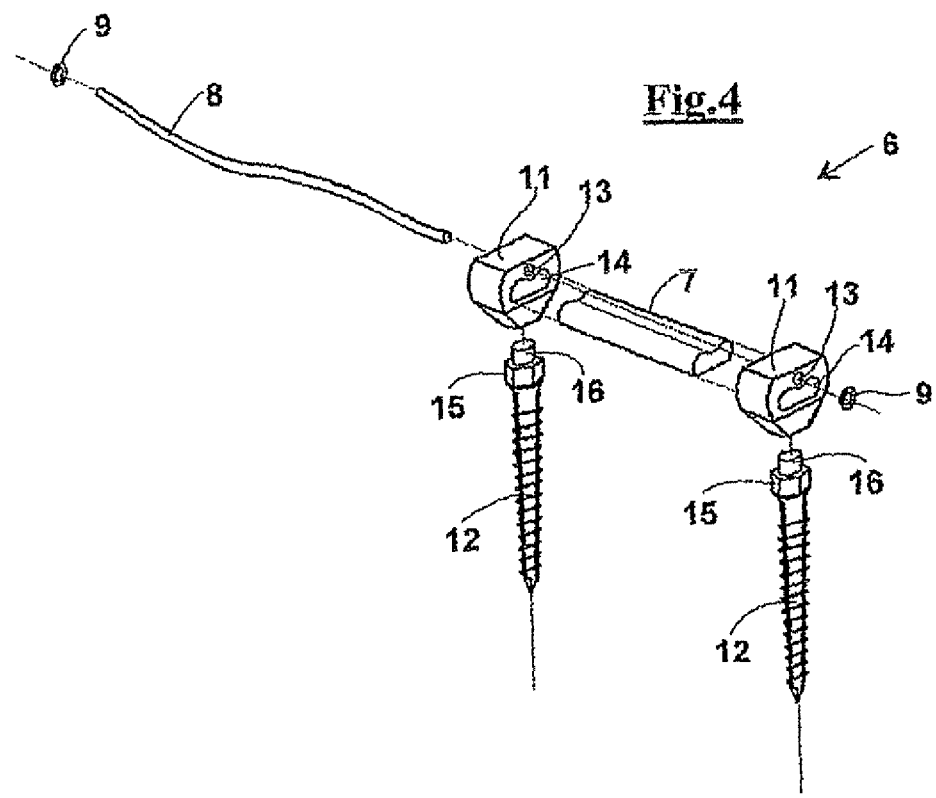
FIG. 4 shows an exploded view of a stabilizer according to the invention.

FIG. 4 shows an exploded view of a stabilizer 6 according to the invention, comprising two screws 12 separate from two heads 11 having two openings 14 adapted to house and engage with the ends of a block 7, and a through hole 13 adapted to let a flexible resilient tie-member 8 to pass through, which can be fixed on said heads 11, once threaded in the hole, by means of two deformable rings 9 connected to the ends of the tie-member.

Figure 5:
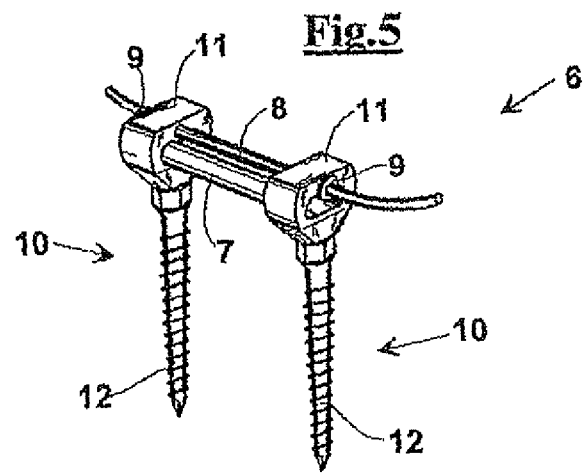
FIG. 5 shows a preferred exemplary embodiment of such a stabilizer.

In FIG. 5, the above described stabilizer is shown mounted, as it is when it is mounted on the vertebrae not shown in the figure.

FIG. 6 shows a cross sectional view of a vertebral dynamic stabilizer as described in FIGS. 2-5, with heads 11, with the relative block 7 and tensioned wire 8, which the surgeon has pre-mounted before applying it to the corresponding screws 12, previously implanted in the vertebrae. The block has been previously cut to a suitable length adapted to set a determined distance between the screws. The two heads 11 are then arranged, aligned and distanced from the block, whose ends engage with and are housed by the respective openings 14. The wire tie-member 8 is suitably blocked in a direction making a first enlargement, so that the wire does not pass further through one of the holes 13 of heads 11. Then the wire is tensioned and blocked also in the other direction making a second enlargement, so that the wire does not pass further through the other hole 13 of head 11.

Then, the surgeon starts the operation by arranging screws 12 in the vertebrae. Once implanted, the screws will be at a distance less than a desired distance, since the operation is necessary because certain vertebrae are too close to one another, owing to known pathologies. The surgeon, then, will bring them to a desired distance, by means of suitable toolings, where the distance is the same that would be imposed by the presence of blocks 7. Then, the surgeon will proceed to snap fitting the pre-assembled parts, that, separately from the operation field had been already prepared so that the heads of the screws are fixed by the blocks at that exact distance. This solution is of huge advantage from a surgical viewpoint and limits to the minimum the duration of the operation on the patient.

Figure 7A:
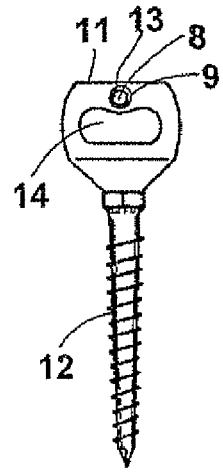
FIGS. 7 A,B show respectively a view and a cross sectional view of an exemplary embodiment of a screw and a head with through hole out of the housing, mounted together of the stabilizer.
Figure 7B:
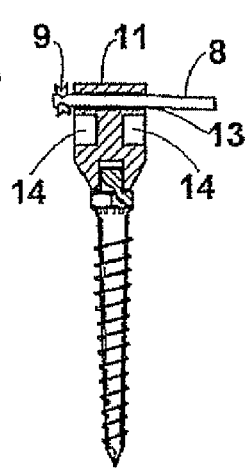

In FIGS. 7 A, B is shown an elevational and a cross sectional view of a screw 12 and head 11 of a stabilizer according to the invention, where screw and head are shown mounted together. Head 11 comprises two openings 14 adapted to house or contain the ends of corresponding blocks not shown, a through hole 13, out of openings 14, adapted to house a tie-member 8 blocked by a deformed ring 9, a housing 17 adapted to house a head 16 of screw 12.

Figure 8A:
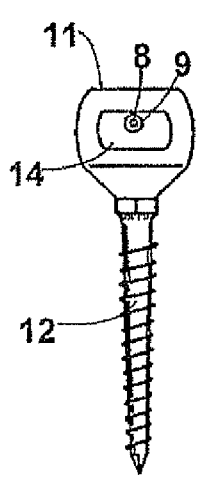
FIGS. 8 A,B show respectively a view and a cross sectional view of another exemplary embodiment of a screw and a head, with through hole in the housing.
Figure 8B:
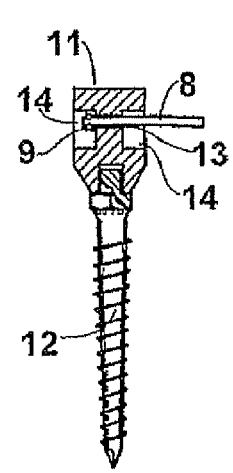

Similarly, in FIG. 8 A-B another exemplary embodiment is shown of screw 12 and head 11, where head 11 comprises a through hole 13 between openings 14, so that the end of the tie-member 8 remains operatively hidden in the above described openings 14, with deformed ring 9.

Figure 9:
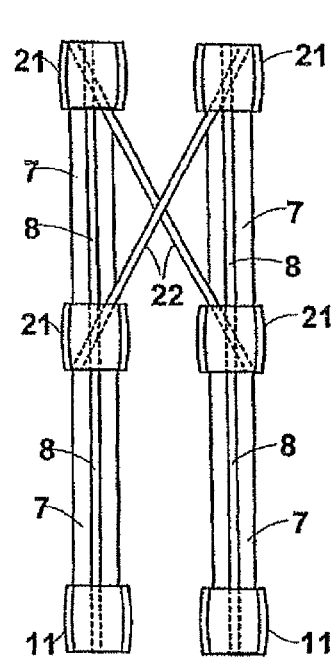
FIG. 9 shows a front view of an example of application of three vertebral stabilizers with transversal pulling elements arranged between two consecutive vertebrae.

In FIG. 9 an example is shown of two couples of stabilizers 50 and 60 assembled on three vertebrae not shown, where said stabilizers require diagonal pulling elements 22 adapted to transmit forces between two adjacent vertebrae, but in a direction different from the axis of the spine, for stabilizing the vertebrae to limit rotation. The stabilizers 50 and 60, as shown in the previous figures, comprise blocks 7 engaged between the heads 21 and the pulling elements 8.

Figure 10:
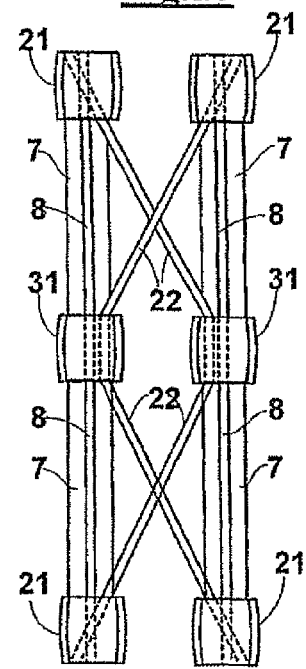
FIG. 10 shows a front view of an example of application of vertebral stabilizers with transversal pulling elements arranged along three consecutive vertebrae.

Similarly, FIG. 10 shows another example of assembling two couples of stabilizers 50 and 60, where diagonal pulling elements 22 are provided on three adjacent vertebrae, not shown.

Figure 11:
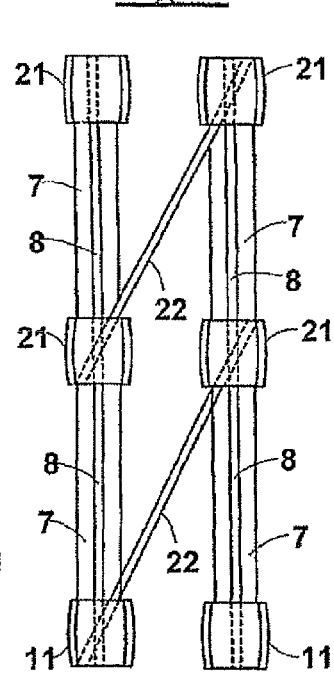
FIG. 11 shows a front view of a further example of application of vertebral stabilizers where two stabilizations of vertebral rotation having the same direction are required.

FIG. 11 shows a front view of a further example of application of vertebral stabilizers where two stabilizations of vertebral rotation are required having the same direction.

Figure 12C:
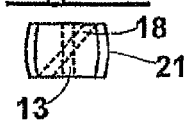
FIGS. 12 A-C and 13 A-C show an elevational and a cross sectional view of two possible exemplary embodiments of screw and head with a second through hole adapted to house a transversal tie-member.
Figure 12A:
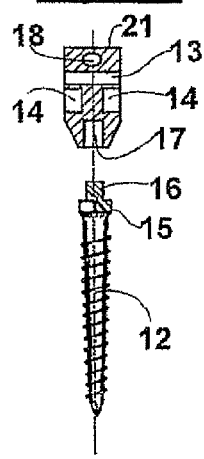
Figure 12B:
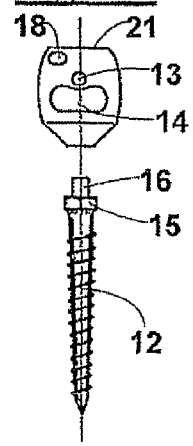

FIGS. 12 A-C show an elevational view and a cross sectional view of a possible exemplary embodiment of screw 12 and head 21, which, besides having a through hole 13 for a longitudinal tie-member not shown, has a second through hole 18, adapted to house a transversal tie-member not shown in the figure. In particular, the axis of hole 18 is incident with the axis of hole 13 in a point belonging to the axis of screw 12, so that the forces applied to head 21, by the pulling elements not shown, do not generate torque actions about axis said screw 12.

Figure 13C:
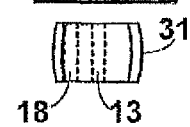
Figure 13A:
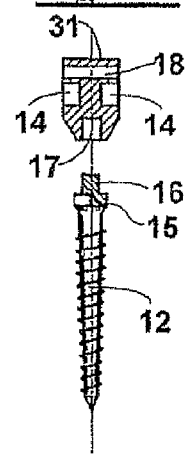
Figure 13B:
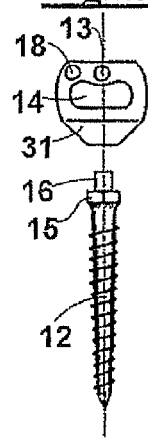

Similarly, FIGS. 13 A-C show, in a cross sectional and elevational view, a screw 12 with a head 31, having in addition to through hole 13, a second through hole 18 parallel to first hole 13, adapted to house a diagonal tie-member 22 as shown mounted in FIG. 10.

In FIG. 14 a perspective view is shown of a possible exemplary embodiment of a block 7, having a channel 41 for passage of a tie-member not shown in the figure.

Figures from 15 to 22 show different alternative exemplary embodiments of a block according to the invention. In particular, FIGS. 14 and 15 refer to a block 7 substantially parallelepiped, having a channel 41 for a longitudinal tie-member 8. FIGS. 16 and 17 show two further exemplary embodiments of a block 7 having a cross section consisting of two substantially cylindrical portions having two opposite channels 41 and 42. FIG. 7 shows a cross sectional view with two semicylinders 45 and 46 distinct from a channel 41 for tie-member B.

FIGS. 20 and 21 show two exemplary embodiments with half circular crown cross section blocks 47 with a channel 41 for tie-member 8. A further exemplary embodiment is shown in FIG. 22 where block 7 comprises two parallel distinct cylinders 48, parallel to tie-member 8.

Notwithstanding in the description reference has been made to the solution of heads 11 of screws 12 separable from each other, this solution is to be considered an advantageous but not limitative function.

Furthermore, notwithstanding in the description reference has been made to wire 8 located out of block 7, it is also possible that block 7 is pierced and the wire passes through it.

FIG. 23 shows one alternative exemplary embodiment of stabilizers of stiff type 50 according to the invention, applied to a spinal column 4, in particular, to consecutive vertebrae 1, 2, 3, having stiff blocks 49 mounted between heads 11 and locked to them.

In FIG. 24, instead, a hybrid stabilizer is shown, according to the invention, which uses a stiff stabilizer 50 associated to a dynamic stabilizer 150 having an elongated resilient block 7 with resilient flexible tie-member 8. In particular, stabilizers 50 and 150 comprise, to this purpose, heads 11 for fixing respectively stiff blocks 49, and elongated resilient blocks 7 with resilient flexible tie-member 8 blocked as described hereinafter.

With reference to FIGS. 2, 4, central head 11 can be a universal head, suitable to stiff connections, and to resilient connections, and to both, i.e. hybrid connections, which serve as "trait of union" for both.

Figures from 25 to 28 show the "modular" aspect of the stiff vertebral stabilizer 50 according to the invention, mounted on two adjacent vertebrae 1 and 2. This stabilizer 50 comprises two screws 12 applied respectively to vertebrae 1 and 2, each'screw 12 supporting a respective head 11, which has one or two opposite openings 14 for engagement of the ends of block 49. Heads 11 have a hole 57 for locking the block by a small screw 53. In particular, small screw 53 enters transversally in the opening 14 and penetrates stiff block 49, made of metal for example of titanium, to ensure an interference that avoids an extraction by accident.

In particular, each head 11, like in the cases described above and in FIG. 28, has a housing 17 adapted to snap engage the end 16 of screw 12. This feature allows also to interchange easily head 11 by an operation located and of convert a dynamic stabilizer into a static stabilizer or vice-versa, or in an hybrid stabilizer, without unscrewing the screws already implanted in the vertebrae.

The same can be said when one of the two heads 11 is of hybrid type, i.e. it can receive on one side a stiff block 49 and on the other side a resilient block 7.

As shown in FIG. 26, where a cross sectional view is illustrated of two stabilizers 50 applied to two adjacent vertebrae of a spinal column, screws 12 have to be implanted, in a known way, and remain completely in the bone and far from the axis of the spinal column, avoiding thus the risk of affecting the bone marrow. In FIG. 25, each head 11 is shown having opening 14.

As shown in detail in FIGS. 27 and 28, block 49, having ends 51 and 52 retained by small screws 53 in respective openings 14 of two heads 11, has a length substantially the same as the predetermined distance between screws 12 and is adapted for a positive engagement with them. This way, stabilizer 50 has the advantages of modularity and ensures an appropriate stiffness, as can be necessary for certain pathologies of the spine. The heads of the screws can be made in the many ways indicated in FIGS. 29 to 32.

Figure 29:
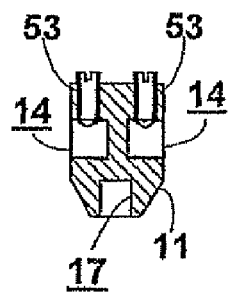
Figure 30:
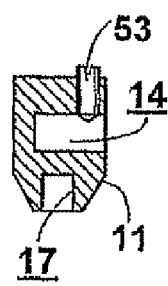
Figure 31:
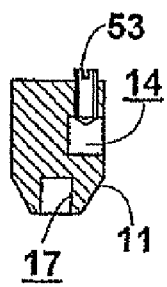

FIGS. 29 to 32 show indeed in cross sectional views some possible exemplary embodiments of a head of a screw according to the invention, with one or two openings or recesses adapted to fasten a stiff block. FIG. 29 shows a head 11 of a screw having two opposite openings 14, which may sometimes be described as recesses, with respective fastening screws 53. This head allows for connection of two stiff blocks not shown to a same vertebra. FIGS. 30 and 31 show two exemplary embodiments of a head 11 having a single opening 14 respectively longer and shorter, having a fastening screw 53.

Figure 32:
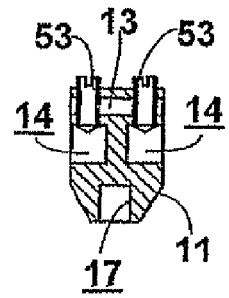

FIG. 32 shows a head 11 of a screw according to the invention having two opposite openings 14 with respective fastening screws 53 corresponding to stiff blocks not shown, and a through hole 13 for passage of a resilient flexible tie-member not shown. This exemplary embodiment is related either to the use of head 11 for fastening two stiff blocks 49 using recess 14 and the screws 53, or alternatively, to connect a resilient block 7 with a flexible tie-member 8 passing through hole 13, without using fastening screws 53.

FIGS. 33, 34 and 35 show a head 11 capable of supporting at the same time a stiff block 49 and a resilient block 7 compressed by a resilient flexible tie-member 8, forming a hybrid stabilizer. The stiff block 49 is connected by screw 53 and flexible tie-member 8 with screw 54. Hole 13 is advantageously curved for allowing a quick introduction of the tie-member 8 from a side face of the head.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is fox the purpose of description and not of limitation.

What is claimed is:

1. A vertebral stabilizer comprising:
   an elongated block having two ends and a length extending between said two ends;
   at least two screws adapted to be put in vertebrae, each of said at least two screws having a head;
   means external to said elongated block for keeping said block compressed between the at least two screws in order to keep said screws at a distance from each other, wherein said means for keeping said block compressed comprises a resilient flexible tie-member coupled to the heads wherein said heads are separated from said screw, said heads and said screws being componible together by engagement means provided between said heads and said screws.

2. The vertebral stabilizer, according to claim 1, wherein said engagement means comprises a connection selected from the group of connections consisting of:
   a click engagement comprising resilient engagement means;
   an engagement with threaded surfaces;
   screws;
   a bayonet coupling;
   a retainer means.

3. The vertebral stabilizer according to claim 1, comprising a resilient flexible tie-member capable of bearing a tension, wherein said heads have a first through hole and said tie-member is stretched between said heads of said two screws.

4. The vertebral stabilizer according to claim 1, wherein said heads have at least one hole and at least one housing at one end of said block, said at least one hole and said housing being made in said heads such that said block is kept compressed between said heads, said block having its ends engaging with the respective housings in order to keep said screws at the distance from each other.

5. The vertebral stabilizer, according to claim 3, wherein said first through hole is made in said head and said block has an open longitudinal channel adapted to receive said tie-member parallel to said block.

6. The vertebral stabilizer, according, to claim 3, wherein said first through hole is obtained in said head outside of a housing.

7. The vertebral stabilizer, according to claim 3, wherein said heads have two housings made on two opposite faces of said heads for engagement of the block.

8. The vertebral stabilizer, according to claim 3, wherein means are provided for fastening to said heads said resilient flexible tie-member with respect to said first hole or said resilient transversal tie-member to a second hole.

9. The vertebral stabilizer, according to claim 8, wherein said fastening means are adapted to make an enlargement on the wire and wherein said fastening means are selected from the group of fastening means consisting of:
   at least one deformed ring clamped about said wire, said ring penetrating partially in the cross section of said wire when plied;
   a tubular element deformable by compression;
   a deformable element having teeth capable of penetrating in the cross section of said wire when said element is squeezed;
   a snap-hook that can be clamped on said wire;
   a knot;
   an enlargement made by plastic deformation of the wire.

10. The vertebral stabilizer, according to claim 8, wherein said fastening means comprises at least one screw gripping said wire.

11. The vertebral stabilizer, according to claim 3, wherein said elongated block has shape selected from the group of shapes consisting of:
   a prismatic body having a substantially rectangular base with a longitudinal channel made on an outer side surface;
   a prismatic body having a substantially rectangular base with a longitudinal channel made on both larger side surfaces;

a prismatic body having a base substantially as half circular crown;

two prismatic bodies parallel to each other, in particular, substantially cylindrical, connected by a narrow strip;

two prismatic bodies parallel to each other, substantially cylindrical, separated from each other.

12. The vertebral stabilizer according to claim 3, wherein said hole for passage of resilient flexible tie-member is made between a front face, in line with said block, and a face side, for introducing said wire from a side face.

13. A vertebral dynamic stabilizer comprising:

an elongated block, having two ends and a length extending between said two ends;

a screw adapted to be put in a vertebra, said screw having a head having a first through hole and at least one housing at one end of said block, a resilient flexible tie-member capable of bearing a tension; wherein said first through hole and said housing are made in said head such that said block is kept compressed between two of said heads, said block having its ends engaging with the respective housings in order to keep said screws at a distance from each other, said tie-member being stretched between said two heads and external to said block.

14. The vertebral dynamic stabilizer according to claim 13, wherein the resilient flexible tie-member is a wire.

15. The vertebral body dynamic stabilizer according to claim 14, wherein the resilient flexible tie-member is coupled to said head by at least one deformable ring clamped about said wire.

16. The vertebral body dynamic stabilizer according to claim 13, wherein said screw is removably coupled to said head.

17. An apparatus, comprising:

at least two fasteners each adapted to be put in a vertebrae, each of the fasteners having a head with at least one hole;

a compressible block having two ends wherein one end of the compressible block is coupled to the hole of one fastener and the other end of the compressible block is coupled to the hole of the other fastener to maintain said fasteners at a minimum distance from each other; and a tension member coupled to each of the fasteners, wherein the tension member is in tension to maintain the compressible block in compression such that the compressible block maintains said fasteners at the minimum distance.

18. The apparatus of claim 17 wherein at least one of the fasteners is removably coupled to the heads.

19. The apparatus of claim 17 wherein the head comprises at least a second hole and the tension member is coupled to the second hole.

* * * * *